United States Patent [19]

Lawrence, Jr. et al.

[11] Patent Number: 4,499,687

[45] Date of Patent: Feb. 19, 1985

[54] HYBRID BRASSICA SEED PRODUCTION

[75] Inventors: Robert H. Lawrence, Jr., Boulder, Colo.; Phillip E. Hill, Gilroy, Calif.

[73] Assignee: Agrigenetics Research Associates Limited, Boulder, Colo.

[21] Appl. No.: 462,416

[22] Filed: Jan. 31, 1983

Related U.S. Application Data

[63] Continuation-in-part of Ser. No. 435,333, Oct. 19, 1982, abandoned, which is a continuation of Ser. No. 169,874, Jul. 17, 1980, abandoned.

[51] Int. Cl.$^3$ ............................................. A01G 1/00
[52] U.S. Cl. ...................................................... 47/58
[58] Field of Search ............................. 47/58, DIG. 1

[56] References Cited

U.S. PATENT DOCUMENTS 4,381,624  5/1983  Lawrence et al. ...................... 47/58

Primary Examiner—Robert E. Bagwill
Attorney, Agent, or Firm—Pennie & Edmonds

[57] ABSTRACT

A process for the production of high purity hybrid Brassica seed, comprising (a) selecting a heterozygous, maximally self-incompatible parent plant, (b) cloning said selected plant to produce a first cloned parental line, the plants of which are both maximally self-incompatible and maximally clonal-incompatible, (c) crossing plants of said parental line with plants of a second parental line, and (d) collecting high purity hybrid seed from said first cloned parental line. The second parental line may also have been obtained by cloning a second maximally self-incompatible plant to obtain a second cloned parental line, the plants of which are both maximally self-incompatible and maximally clonal-incompatible. The second parent plant may be homozygous or heterozygous. The high purity hybrid seed may be collected from said second maximally self-incompatible cloned parental line or alternatively from both first and second maximally self-incompatible cloned parental lines.

9 Claims, No Drawings

HYBRID BRASSICA SEED PRODUCTION

CROSS-REFERENCE TO RELATED APPLICATION

This application is a continuation-in-part of application Ser. No. 435,333, filed Oct. 19, 1982, which is a continuation of application Ser. No. 169,874 filed 7-17-80 (both abandoned).

BACKGROUND OF THE INVENTION

This invention relates to the production of high purity $F_1$ hybrid seeds in those species of the genus Brassica which exhibit strong self-incompatibility, and more particularly concerns a method of producing high purity $F_1$ hybrid Brassica seeds in high yield without the prior necessity of labor-intensive bud pollination to produce nearly homozygous, inbred parent plants.

The current procedures used to produce such $F_1$ hybrid Brassica seeds are widely recognized as having serious limitations, both in terms of cost and as regards seed purity. They all require the establishment and provision of stable, sib-incompatible and self-incompatible, nearly homozygous, parental breeding lines, which are available after repeatedly selfing to generate inbred lines. Because Brassica hybrid seed production systems based on the self-incompatible traits of Brassica must utilize strongly self-incompatible plants (an individual plant which will not readily pollinate itself), inbreeding to develop and maintain the parental lines can only be effected by labor intensive techniques, such as bud pollination.

These difficulties in developing and maintaining the parental inbred breeding lines are reflected not only in high hybrid seed cost as a result of the labor cost, but, in practical effect, have required that the breeding lines be maintained in foreign, low-labor-cost countries.

Moreover, the parental lines are of necessity highly inbred, and in Brassica the plants have low vigor, resulting in low $F_1$ hybrid seed yields.

When making hybrid seed from two parental lines, one of three approaches is used. In the first approach, the flowers in one line are emasculated by hand, and are fertilized with pollen from the crossing line. This manifestly is labor intensive, and consequently expensive. A second approach, widely used on a commercial scale, avoids emasculation. Two inbred parental lines, where one or both lines is sib-incompatible (does not readily pollinate with its siblings) as well as self-incompatible (nearly incapable of fertilizing itself) are crossed by natural pollination. Hybrid seed is collected only from the sib-incompatible breeding line. In the usual case, where one inbred is sib-incompatible, a high ratio, typically 3:1, of the sib-incompatible inbred to the normal inbred is used, and only the seed produced on the sib-incompatible inbred is harvested for sale. Ideally, if both inbreds are sib-incompatible, a 1:1 ratio of the two can be used, and, due to the reciprocity rule of genetics, the entire seed crop can be harvested.

A third approach, also widely used commercially, involves the use of male sterility in the maternal seed parent to prevent self-pollination. Hybrid seed is thus collected from the maternal seed parent. However, utilization of self-incompatibility is superior to that of male sterilty in view of the $F_1$ seed yield since the $F_1$ seed can be obtained from both self-incompatible parental lines.

While the sib-incompatible technique for $F_1$ hybrid Brassica seed production avoids many of the difficulties of emasculation, a number of problems are encountered in practice. One such problem is that large populations of inbreds are used, and these tend to drift genetically due to their being sexually reproduced.

An especially serious seed quality problem arises with the use of sib-incompatible hybrid techniques. If a "misnick" (poor timing between the two inbreds in their going into inflorescence) occurs, some sibbing takes place on the ostensibly sib-incompatible parent, giving rise to inbreds being present in the seed crop. This may result in the seed not being of sufficiently high purity to comply with present day labeling laws, which mandate that a hybrid seed contain at least 95% of the designated hybrid.

And finally, the development of a sib-incompatible inbred normally requires at least about 10 years of inbreeding.

It is known in the art to vegetatively propagate various Brassicas, including self-incompatible Brassicas, and further, to maintain such inbred parental lines for purposes of hybrid seed production. The use of cloning to maintain inbred lines overcomes the above-described labor-intensive techniques.

OBJECTS OF THE INVENTION

Accordingly, an object of the invention is to provide a method of commercially producing high purity Brassica seed while avoiding the prior difficulties of developing and maintaining inbred parental breeding lines by seed.

Another object is to provide such seed without requiring labor-intensive bud pollination.

Still another object is to provide a method for producing high purity hybrid Brassica seeds which combines the low labor cost of the sib-incompatible hybrid technique with the seed purity of the manual emasculation technique.

Still a further object is to provide a method of making high purity hybrid Brassica seed without requiring the elaborate and expensive maintenance of self-incompatible, homozygous, parental breeding lines.

Another object is to maintain consistently high purity, and consistently high quality hybrid Brassica seed, giving a better, constant quality product to the customer year in and year out.

Still another object is to provide a method for commercially producing hybrid Brassica seed while retaining local control of the breeding lines.

Yet another object is to avoid the genetic drift associated with sexual propagation techniques for maintaining the breeding lines, and therefore to have higher quality commerical seed production.

Another object is to avoid the problems of low vigor and poor seed production inherent in use of highly inbred lines.

A further object is to produce new hybrids from one or both heterozygous parents, and yet have the hybrid plants be satisfactorily uniform phenotypes. Still another object is to produce superior new hybrids of greater genetic diversity.

An overall object is to provide a method for economically and rapidly producing high purity hybrid Brassica seed and new improved hybrids.

Further objects will become apparent from the description of the invention which follows.

The methods of the present invention are applicable to all members of the genus Brassica which exhibit high self-incompatibility, and may be vegetatively propagated or cloned.

Briefly, in accordance with the invention, high purity hybrid Brassica seed is produced commercially by natural cross pollination of two parental breeding lines, one (or both) of which is (are) obtained by cloning a maximally self-incompatible heterozygous individual parent plant. The resulting cloned parental line is comprised of plants which are maximally self-incompatible and maximally incompatible with other plants cloned from the same parent. This property of maximum incompatibility among plants cloned from the same parent plant is referred to hereafter as "clonal-incompatibility".

Several significant advantages flow from practice of the methods of the invention. The prior need for inbreeding is avoided by selecting for the cloning a heterozygous plant which exhibits the maximum degree of self-incompatibility, thereby producing clones of that plant which are maximally self-incompatible and maximally clonal-incompatible as well. Thus, because the original parental plants are chosen for being self-incompatible, the clones are each "self" to each other and thus are clonal-incompatible. Generally, clonal-incompatibility provides stronger incompatibility than sib-incompatibility. Consequently, when one cloned maximally self-incompatible parental line is natually cross-pollinated with another parental line, only pollen from the latter can fertilize the first line. As a result, seed from the first line is of a uniformly high hybrid purity, with little or no likelihood of self-fertilization (inbreeding). If both of the parental lines are cloned parents (each selected for being maximally self-incompatible), then natural cross pollination of the two resulting lines gives a seed crop obtainable from both lines.

The cloning technique has several major advantages over pre-existing methods of making hybrid seed. First, it eliminates the need for the elaborate and expensive procedures for establishing and maintaining self-incompatible, nearly homozygous, parental breeding lines, which heretofore have required laborious manual bud pollination. Second, by cloning optimal parents, the clones retain the optimum genetic characteristics of the parents. Further, when the cloning is effected according to the optimum practice of the present invention, the original-parent-derived hybrids are genetically equivalent to the cloned-parent-derived hybrids.

Fourth, because the parental "lines" are numerically limitless (not limited to the available inbreds), the plant breeder has available breeding "lines" of limitless genetic diversity. As a consequence, hybrids can be produced with characteristics that are equal to, or superior to hybrids that are derived from the conventional crossing of highly inbred homozygous parents.

Finally, because one or both of the original parents is heterozygous, the parent line (or lines) used for commercial seed production can be vigorous and high yielding hybrids instead of low-vigor inbreds. Consequently, the hybrid seed yield will be high and cost of production should be lower.

The cloning techniques prepared for use herein are similar to those developed for other purposes or for other plant species. See Encyclopaedia Britannica, Macropedia, "Tissue Culture," "Tissues and Fluids, Plant," "Horticulture, Plant Breeding," "Fruits and Fruit Farming," and "Vegetables and Vegetable Farming," together with articles cited therein. State-of-the-art technology is reviewed in "Propagation of Higher Plants Through Tissue Culture," Proceedings of International Symposium, University of Tennessee, Knoxville, Apr. 16–19, 1978 (Technical Information Center, U.S. Department of Energy, National Technical Information Service, U.S. Department of Commerce, Springfield, Va. 22161, Conference T-80411); E. Thomas and M. R. Davey, "From Single Cells to Plants," (Wykenham Publ. 1975); and D. N. Butcher and D. S. Ingram, "Plant Tissue Culture," (Camelot Press, 1976). A pertinent literature reference is W. C. Anderson and J. B. Carstens, "Tissue Culture Propagation of Broccoli, *Brassica oleracea* (Italica Group) for use in $F_1$ Hybrid Seed Production," J. Am. Soc. Hort. Sci., 102(1), 69–73 (1977), and references cited therein, together with references in the Example below. Patent references include Kadkade U.S. Pat. No. 4,038,778, McCormick Brit. Pat. No. 1,387,821, Sibi U.S. Pat. No. 4,003,156, Routien U.S. Pat. No. 2,747,334, Tuckacs U.S. Pat. No. 3,009,289, McDade U.S. Pat. No. 3,514,900, Corlett U.S. Pat. No. 3,683,550, Gudin U.S. Pat. No. 3,816,960, Stottlemeyer U.S. Pat. No. 3,821,864, Carlson U.S. Pat. No. 3,832,801, Patterson, U.S. Pat. No. 3,861,079, Gudin U.S. Pat. No. 3,955,317, Boxus U.S. Pat. No. 3,972,146, Seibert U.S. Pat. No. 4,052,817, and Kadkade U.S. Pat. No. 4,060,933.

Since tissue culture propagation is preferably employed for the cloning, that part of an individual plant is selected which is capable of being developed under tissue culture conditions to increase in number and then form an entire plantlet that can be transplanted to soil and ultimately to the field. Such plant parts as axillary buds or shoot apices (e.g., for cabbage), curds (e.g., for cauliflower), root and stem tips, or other plant parts that can be propagated without the risk of detrimental genetic change, may be used.

Depending upon the species, different in vitro techniques may be used. See, for example, the preferred method for cauliflower as described in the example which follows, a method for broccoli described by Anderson and Carstens (J. Amer. Soc. Hort. Sci. 102 (1), 69–73 (1977), and the cloning protocol for cabbage (Application Ser. No. 169,875, filed July 17, 1980).

For purposes of illustration, the invention is described hereinafter for cauliflower. It is to be understood that this does not constitute a limitation of applicability of the present method to this species. Rather, the present invention may be practiced with any species of Brassica which exhibits high self-incompatibility, and may be vegetatively propagated or cloned. The methods of the invention are particularly suited to cauliflower, cabbage, broccoli, Chinese cabbage and turnips.

SCHEDULE (CAULIFLOWER)

A typical schedule for the commerical production in California of high purity hybrid cauliflower seed is presented below. Individual operations conducted according to the schedule are also discussed.

(1) First Year

In the fall of the first year, a row of about 100 feet of genetically diverse, heterozygous plants is sown. These will be thinned. Conventional farming practices are followed and the remaining plants are permitted to grow to full market maturity, which requires between about 60 to 120 days. Alternatively, the plants can be started in pots to facilitate subsequent transfer to the greenhouse.

In the spring of the first year, when the plants have reached market maturity, a number of the plants with desired characteristics are selected as parent plant candidates. These parent plant candidates are labelled, as by physically tagging the plant. Parent plant candidates with high self-incompatibility are selected after transplantation to a greenhouse. Simultaneously, part of each parent candidate plant is removed for vegetative propagation by in vitro cloning techniques. The transplants are grown to flower maturity and the inflorescences are bagged to determine the seed set. Those plants with the least seed set (i.e., those that are the most strongly self-incompatible) are then selected as the parent plants to be cloned and used in the production of hybrid seed. Alternatively, the strength of self-incompatibility may be measured by pollen tube counts in the pistil as described by van Hal (Brassica meeting of Eucarpia: 1968; Nat. Veget. Res. Sta., 32–33 (1968)). Parent plant candidates with low self-incompatibility and the tissue cultures therefrom are discarded at this stage.

It is also possible, using pollen collected from parent plant candidates, to make test crosses to assess the ability of the parent plant candidates to generate hybrids in specific crosses having an optimal combination of desired traits. Such tests are readily undertaken with other selected heterozygous transplanted individuals, but can be performed where the second parent in the cross is an inbred strain.

Explants of the curds produced from the strongly self-incompatible parent plants are taken for vegetative cloning. The closing procedure, detailed below, is conducted organogenetically, under suitable tissue growth conditions in an aseptic nutrient medium. Alternatively, all or part of the explants may be stored, as for example under cryogenic conditions, e.g. Seibert M. S. Pat. No. 4,052,817.

Thus, based on the tests used to determine which individual parent plant candidates have the strongest self-incompatibility, a number of parent plants is identified and propagated by vegetative cloning to form cloned parent lines. About 10 plants clonally derived from each original parent plant are grown. The transplanted parent plants are at the same time used in pairwise crosses for the determination of which pairwise crosses are best used in the production of hybrids with high yield and uniformity. In the summer, seed from the pairwise crosses of the parent plants selected on the basis of their self-incompatibility is harvested and vegetative propagation of the cloned parent lines is continued. Plants are regenerated in the greenhouse from each cloned parent line and, when mature, these plants are used for a second test of self-incompatibility of each cloned parent line. In addition, these regenerated plants may be used in additional pairwise crosses to identify other hybrids with high yield and uniformity.

(2) Second Year

Seeds harvested in the summer of the first year from the pairwise crosses of the parent plants are planted and the plants derived therefrom are evaluated for uniformity and yield during the life cycle. Those combinations of parent plants giving the greatest uniformity of desired characteristics and maximum yield are recorded and the cloned parent lines derived from those parent plants are further vegetatively propagated and regenerated into plantlets. Sufficient plantlets are produced by in vitro cloning techniques to allow the initiation of a pilot field study in the fall of the third year.

(3) Third Year

In the fall, plantlets of the cloned parent lines derived from the two original parent lines which, when crossed together, produced a hybrid with maximum uniformity of desired characteristics and highest yield, are planted in the field for a pilot study. The plantlets of these cloned parent lines are planted in close proximity to each other but are isolated from chance fertilization by pollen from extraneous plants. Crossing of the lines occurs by natural pollination. Hybrid seed from this pilot study is harvested in the summer of the fourth year.

(4) Fourth Year

The hybrid seed harvested in the summer of the fourth year is planted in the fall of the fourth year. As these hybrid seeds progress through their life cycle, they are evaluated for uniformity of desirable genetic characteristics and for high yield. These genetic characteristics should conform to the genetic characteristics observed in the hybrid plants derived from the corresponding original parent plants. As soon as it has been ascertained that the uniformity and yield of the original cross and of the pilot study are maintained, then a large scale vegetative propagation of the two cloned parent lines is undertaken in order to carry out former's trials and climate trials in the fifth and sixth years.

The pilot field study can be extended to estimate the uniformity of desirable characteristics of the hybrid plants and high yield under different climatic conditions by conducting multiple pilot studies in a number of geographical situations.

(5) Fifth Year

In the fall of the fifth year, the commercial hybrid production fields are set out. A plant density of about 8,000 plants per acre is used, and an equal number of plants from each of the parent lines is used. These are then naturally cross-pollinated by insects. Seed from these plants is harvested, and is ready for sale. As indicated previously, since each of the cloned parent lines is clonal-incompatible, and since the reciprocal crosses have been tested for genetic equivalency, the entire seed production is marketable.

VEGETATIVE PROPAGATION OF PARENTAL LINES

The technique of tissue culture, or vegetative propagation, permits the regenerative cloning of whole plants by a procedure which does not require seeding, or sexual reproduction. In the procedure of the present invention, cauliflower curds are propagated in vitro in a sterile gel containing a nutrient medium along with plant growth hormones.

Any of a variety of basal nutrient media may be employed. While the one of choice is essentially that of Murashige and Skoog (identified below), others have been suggested by Skoog, Heller, Knop, Gamborg, White, and Street.

The basal medium usually contains (1) inorganic ions, both major and minor, required to maintain fluid balance and to act with certain enzymes, (2) energy sources, typically sucrose, which also provide a major source of carbon atoms for the formation of certain cell constituents, (3) nitrogen-containing compounds, mainly one or more amino acids, (4) essential vitamins and traces of certain metal ions, (5) plant growth hormones, as more fully developed below, and various other constituents.

The technique of tissue culture as a method of vegetative propagation has been elaborated upon in a number of the literature articles referred to earlier.

Fundamentally, the tissue culture protocol involves the removal of a part of the plant (explant) under sterile conditions, and placing it in an appropriate nutrient medium for growth. For cauliflower, the preferred nutrient medium is an agar gel, which permits propagation under comparatively conservative techniques in order to avoid genetic alteration.

In the preferred approach, cauliflower curds are excised from the selected plants and are treated in a three-stage tissue culture protocol. These stages optimize plant shoot establishment, multiplication, and rooting, by controlling the content of plant hormones in each of the stages.

Two hormones have been found especially useful for proper growth and development in culture. Auxins, which affect cell elongation, influence such processes as cell enlargement, leaf and organ separation, budding, flowering, fruit set and growth, and root initiation and development. The other group of hormones, cytokinins, influence the stimulation of cell division and proper formation and development of organs. A low auxin but high cytokinin content gives rise to shoot development; a high auxin but low cytokinin content gives rise to root development.

For cauliflower, the first stage in the protocol of vegetative propagation is to establish a shoot culture from meristematic tissue of cauliflower curds. This has been found to be effected best in an agar-based nutrient medium that is comparatively high in auxin (e.g., 2.5–10 mg/l) but low (e.g., 0.5–2.5 mg/l) in cytokinin. Thus, curds placed in the first stage propagation medium develop individual shoots.

After a period of growth in the first stage medium approximating two or three weeks, the shoots can be isolated for multiplication in the second stage.

When it is desired to multiply the shoots in the second stage, shoot explants are placed in a second nutrient medium. This contains a reduced content of auxin (e.g., 0.5–2.5 mg/l) and a much higher content (e.g., 2.5–10 mg/l) of cytokinin, the latter of which is conducive to multiplication or proliferation. This medium contains a phosphate, and with the composition described below gives a multiplication rate of about 13 shoots every three weeks or so.

The shoots produced in the second stage can be multiplied indefinitely or, if desired, can be stored. Cryogenic storage techniques have not yet been perfected for cauliflower, but similar techniques have been used for other plant species; see Seibert U.S. Pat. No. 4,052,817, suggesting storage below minus 70° C. after controlled freezing and subsequent thawing. Seibert also suggests a variety of cryoprotectants. Optimally, storage at liquid nitrogen temperature is preferred.

The shoots from the second stage lack adequate root development, and for this reason are placed in a third, or rooting, stage containing low auxin (e.g., 0.5–2.5 mg/l) and very low cytokinin (e.g., 0.001–0.5 mg/l).

After approximately two or three weeks, sufficient root development is observed to permit the propagated shoots to be transplanted for ultimate growth to maturity in the field. A hardening off treatment, consisting of maintaining the plantlets in a sterile (peat/vermiculite mixture) potting medium under conditions of mist and high humidity, prepares the plantlets for transplanting.

EXAMPLE (CAULIFLOWER)

This Example illustrates in vitro propagation of cauliflower, *Brassica oleracea*, var. Botrytis.

General Procedure

Using shoots derived from meristematic tissues of cauliflower curds, experiments were carried out to determine the nutritional requirements of shoot development and multiplication from explants for organogenetic clonal propagation.

Tissue culture propagation of Brassica crops is particularly important as an alternative means of maintaining self-incompatible or sib-incompatible inbred parents for $F_1$ hybrid seed production (Anderson & Carstens, 1977). There have been reported instances of in vitro organogenesis and embryogenesis from callus tissue culture of cauliflower (Baroncelli et al., 1973; Pareck and Chandra, Plant Sci. Lett. 11, 311–316 (1978)). However, adventitious shoots originated from meristematic primordia of curds have been most extensively studied for the purpose of clonal propagation (Pow, Hort. Res. 9, 151–152 (1969); Walkey and Woolfitt, J. Hort. Sci. 45, 205–206 (1970). Crisp and Walkey, Enphytica 23, 305–311 (1974); Grout, Plant Sci. Lett. 5, 401–405 (1975)).

Although several reports on in vitro clonal propagation of this crop are available, knowledge of suitable culture media for multiplication of in vitro formed shoots is limited. Therefore, explant clones derived from cauliflower curds were established to determine their hormonal and nutritional requirements in vitro.

Based in part on Murashige's three-step propagation methods (Murashige, 1974), a protocol and medium for cauliflower propagation were developed and are summarized in Table I, below. The procedure was:

Stage 1. Establishment of axenic culture: As noted earlier, curd tissues were employed as initial explants, from which shoots develop and are isolated. The culture medium for this stage utilized a simple basal nutrient gel medium, high in auxin and low in cytokinin, lacking $NaH_2PO_4$, to produce the vegetative shoots for Stage 2 (see Table I, below).

Stage 2. Maximize the rate of vegetative shoot multiplication: Shoots from Stage 1 were isolated and then multiplied in Stage 2. The Stage 2 medium consisted of basal medium, $NaH_2PO_4$, 6 mg/l Kinetin, and 1.0 mg/l indole acetic acid (IAA). The multiplication rate using this medium was about 13 shoots/2 weeks when cultured in 25×150 mm tubes containing 25 ml agar medium. This stage was repeated many times in order to provide the shoots for Stage 3.

Stage 3. Rooting of vegetative shoots: This stage utilized a medium containing 0.1 mg/l Kinetin and 1 mg/l IAA to promote root formation. $NaH_2PO_4$ was excluded from the medium. For the purpose of recovering normal photosynthetic activity in green explants, sucrose concentration was lowered to one half of the basal medium.

The cultures in each stage were kept under light intensity of 2,500 lux provided by (Sylvania) cool white lamps for 16 hrs/day at constant 26°±2° C. temperature.

Preparation of Tissue Explants

Curds were obtained from mature, field-grown cauliflower plants. Tissues were disinfected by a 30 second wash in 70% (v/v) ethanol followed by soaking in 1%

(w/v) sodium hypochlorite for 7 minutes followed by three rinses in sterile water. Curds were further dissected to 2-3 mm size.

TABLE I

Medium Composition[a] for Clonal Propagation of Cauliflower Explants at Three Stages of In Vitro Culture[b]

| Constituents (mg/l) | Stage 1 Establishment | Stage 2 Multiplication | Stage 3 Rooting |
|---|---|---|---|
| Inorganic Salts | | | |
| MS Salts formulation | [c] | [c] | [c] |
| $NaH_2PO_4 \cdot H_2O$ | — | 170 | — |
| Organic Substances | | | |
| myo-inositol | 100 | 100 | 100 |
| Thiamine.HCl | 0.4 | 0.4 | 0.4 |
| Kinetin | 1 | 6 | 0.1 |
| IAA | 3 | 1 | 1 |
| Sucrose | 30,000 | 30,000 | 15,000 |
| Complex Addenda | | | |
| Agar | 7,000 | 7,000 | 7,000 |

[a] pH of medium was adjusted to 5.7 with 0.1 N KOH and/or 0.1 N HCl before autoclaving.
[b] Initial tissue for each culture stage is curds for Stage 1, vegetative shoots for Stage 2, and adventitiously formed shoots for Stage 3. See detailed description of each Stage in the text.
[c] T. Murashige & F. Skoog. "A revised medium for the rapid growth and bioassays with tobacco tissue culture." Physiol. Plant. 15, 473-497 (1962).

Stage 1—Establishment of Axenic Culture

The dissected curds were inoculated to a basal agar medium (Stage 1) which contained Murashige & Skoog salts and the following constituents, in mg/l: IAA (indole acetic acid) 3; Kinetin (6-furfuryl-aminopurine) 1; myo-inositol, 100; thiamine HCl, 0.4; sucrose, 30,000; and (Sigma) agar, 7,000.

At least ten shoot explants were used per treatment. The hormonal and nutritional parameters tested in this investigation were IAA as an auxin, kinetin as a cytokinin, IBA (indole-3-butyric acid) as an auxin, NAA (naphthalene acetic acid) as an auxin, 2iP ($N^6$-$\Delta^2$-isopentenyl adenine) as a cytokinin, adenine sulfate, and sodium phosphate (monosodium form). Cultures were kept under 16 hrs light at 2,500 lux from (Sylvania) cool white lamps at a constant 26°±2° C. Observation was made after two weeks of culture.

The pH was adjusted to 5.7±0.1 using 0.1N HCl prior to autoclaving. Tissue explants were cultured on a 15 ml agar medium contained in 60×15 mm plastic petri dishes. After two to three weeks, vegetative shoots developed from the curd primordia.

After two weeks' culture of curd tissues on the agar medium, meristematic tissues developed into chlorophyllous shoots. Indefinite adventitious shoot multiplication may be achieved by simply propagating individual shoots on basal medium. These shoot explants serve as a stock culture for further experimentation.

Experiments were carried out using a basal medium containing 1 mg/l Kinetin and IAA as a variant. Table II shows the influence of IAA concentration on shoot or root organogenesis from cauliflower shoot explants. The optimum IAA concentration for shoot development was found to be in the neighborhood of 1 mg/l, whereas higher IAA, concentrations were required to stimulate root initiation.

TABLE II

Influence of IAA Concentration on Shoot or Root Induction from Cauliflower Shoot Explants Medium Contained 80 mg/l Adenine Sulfate and 170 mg/l $NaH_2PO_4$. Kinetin at 3 mg/l.
(Variation: ± S.E.)

| IAA (mg/l) | No. of Shoots | No. of Roots |
|---|---|---|
| 0 | 1.7 | 0 |
| 0.1 | 3.1 | 0 |
| 0.3 | 3.2 | 0 |
| 1.0 | 5.3 | 0.6 |
| 3.0 | 3.3 | 0.5 |
| 6.0 | 2.4 | 6.0 |
| 10.0 | 3.0 | 10.0 |

In the next set of experiments, IAA was kept constant at 1 mg/l and Kinetin concentrations were varied from 0-10 mg/l. In Table III, one can see the dramatic effect of Kinetin on both shoot and root organogenesis. Kinetin at higher than 1 mg/l promotes shoot formation, but inhibits root differentiation.

TABLE III

Influence of Kinetin Concentration on Shoot or Root Formation of a Cauliflower Shoot Explant Medium Contained 80 mg/l Adenine Sulfate and 170 mg/l $NaH_2PO_4$. IAA at a constant 1 mg/l.
(Variation: ± S.E.)

| Kinetin (mg/l) | No. of Shoots | No. of Roots |
|---|---|---|
| 0 | 2.4 | 4.7 |
| 0.1 | 2.2 | 5.3 |
| 0.3 | 3.7 | 2.8 |
| 1.0 | 3.1 | 0.2 |
| 3.0 | 3.8 | 0.6 |
| 6.0 | 5.2 | 0 |
| 10.0 | 4.0 | 0 |

Other experiments using other growth regulators such as IBA, 2iP or NAA were conducted (data are not presented). IBA, when combined with IAA, promoted shoot differentiation as effectively as did Kinetin. 2iP was less effective than Kinetin.

A dramatic result was observed when NAA was supplied with either Kinetin, IBA, or 2iP. Large quantities of root hairs were found on the NAA medium, a response not observed in the IAA control.

Table IV summarizes the effect of adenine sulfate (80 mg/l) and $NaH_2PO_4$ (170 mg/l) in the presence of both IAA and Kinetin. For comparison purposes, the effect of IAA or Kinetin alone in the basal medium is also presented. Adenine sulfate appears to inhibit adventitious shoot initiation in cauliflower shoot explants. In contrast, $NaH_2PO_4$ in the absence of adenine sulfate stimulates shoot organogenesis.

Shoots obtained from the axenic culture of Stage 1 were separated from the tissue under sterile conditions, and were then used for Stage 2 multiplication.

Stage 2—Shoot Multiplication

For rapid multiplication of vegetative shoots, the basal medium was supplemented with 170 mg/l $NaH_2PO_4$, 1 mg/l IAA and 6 mg/l Kinetin. See Table I, above. The rate of multiplication was about 13 shoots/2 weeks when a 25 ml agar medium in a 25×150 mm culture tube was used.

Stage 3—Rooting of Vegetative Shoots

The rooting of propagated shoots was enhanced by employing the basal medium with a modification of IAA and Kinetin at 1 mg/l and 0.1 mg/l respectively.

See Table I, above. The low Kinetin concentration promoted root development. For the purpose of recovering normal photosynthetic activity in green explants, sucrose concentration was converted to use half of the basal medium.

TABLE IV

Effect of IAA, Kinetin Adenine Sulfate and NaH₂PO₄ on In vitro Initiation of Shoot or Root of A Cauliflower Shoot Explant
IAA (1 mg/l), Kinetin (3 mg/l), Adenine Sulfate (80 mg/l), and NaH₂PO₄ (170 mg/l) Added to the Basal Medium

| ADDENDA | No. of Shoots | No. of Roots |
| --- | --- | --- |
| IAA | 1.7 | 14.6 |
| Kinetin | 4.6 | 0 |
| IAA + Kinetin | 3.0 | 0 |
| IAA + Kinetin + Adenine Sulfate | 3.6 | 0 |
| IAA + Kinetin + NaH₂PO₄ | 6.5 | 0 |
| IAA + Kinetin + Adenine Sulfate + NaH₂PO₄ | 4.5 | 0 |

Planting of Plantlets

Cauliflower plantlets derived from culture were transplanted to pots containing a peat/vermiculite mixture in a greenhouse.

The plants were hardened off under a mist providing high humidity during the first two weeks after transplantation. This procedure evidently enhances epicuticular wax development, sufficient stem and root development, and full photosynthetic capability as reported elsewhere (Grout, Plant Sci. Lett. 5, 401–405 (1975); Grout and Aston, Hort. Res. 17, 1–7 (1977); Grout and Aston, Hort. Res. 17, 65–71 (1978)). Survival of plants was more than 95%.

The clonal plants developed normal curds after about two months, and flowered at approximately the same time as the plants derived from seeds.

Thus, the present protocol for cauliflower plant propagation provides a potential for large scale propagation of lines for seed production.

We claim:

1. A process for the production of high purity hybrid Brassica seed, comprising:
   (a) selecting a heterozygous maximally self-incompatible parent plant;
   (b) cloning said selected heterozygous maximally self-incompatible parent plant to produce a first cloned parental line, the plants of which are both maximally self-incompatible and maximally clonal-incompatible;
   (c) crossing plants of said first cloned parental line with plants of a second parental line; and
   (d) collecting high purity hybrid seed from said first cloned parental line.

2. A process for the production of high purity hybrid Brassica seed, comprising:
   (a) selecting a heterozygous, maximally self-incompatible parent plant;
   (b) cloning said selected heterozygous, maximally self-incompatible parent plant to produce a first cloned parental line, the plants of which are both maximally self-incompatible and maximally clonal-incompatible;
   (c) crossing plants of said first cloned parental line with plants of a second parental line; and
   (d) collecting high purity hybrid seed from said second parental line, wherein the plants of said second parental line are either self-incompatible and sib-incompatible or self-incompatible and clonal incompatible.

3. The process according to claim 1, wherein said second parental line is obtained by cloning a second maximally self-incompatible parent plant to produce a second cloned parental line, the plants of which are both maximally self-incompatible and maximally clonal-incompatible, and the hybrid seed is collected from one or both parent lines.

4. The process according to claim 3, wherein said second parent plant is heterozygous.

5. The process according to claim 3, wherein said second parent plant is homozygous.

6. The process according to claim 1, wherein said Brassica is cabbage.

7. The process according to claim 1, 2, or 3, wherein said Brassica is broccoli.

8. The process according to claim 1, 2, or 3, wherein said Brassica is cauliflower.

9. The process according to claim 1, 2, or 3, wherein said Brassica is Chinese cabbage.

* * * * *